United States Patent
Schilp et al.

(10) Patent No.: US 8,372,058 B2
(45) Date of Patent: Feb. 12, 2013

(54) SYSTEM AND METHOD FOR CLOSED, DRIP-FREE, AND SECURE TRANSFER OF FLUIDS

(75) Inventors: Michael Schilp, Garching (DE); Oliver Buck, Bayerisch Gmain (DE)

(73) Assignee: Isotopen Technologien Munchen AG, Bad Reichenhall (DE)

( * ) Notice: Subject to any disclaimer, the term of this patent is extended or adjusted under 35 U.S.C. 154(b) by 682 days.

(21) Appl. No.: 12/299,604

(22) PCT Filed: May 2, 2007

(86) PCT No.: PCT/EP2007/003877
§ 371 (c)(1), (2), (4) Date: Jun. 15, 2009

(87) PCT Pub. No.: WO2007/128481
PCT Pub. Date: Nov. 15, 2007

(65) Prior Publication Data
US 2009/0243283 A1  Oct. 1, 2009

(30) Foreign Application Priority Data
May 4, 2006  (DE) .................. 10 2006 020 845

(51) Int. Cl.
*A61M 25/18* (2006.01)
(52) U.S. Cl. ....................... 604/533; 604/905
(58) Field of Classification Search ............ 604/167.03, 604/246, 249, 533, 905
See application file for complete search history.

(56) References Cited

U.S. PATENT DOCUMENTS

| 3,672,226 | A |   | 6/1972  | Reid |
| 5,122,123 | A |   | 6/1992  | Vaillancourt |
| 5,370,636 | A |   | 12/1994 | Von Witzleben |
| 5,393,101 | A |   | 2/1995  | Matkovich |
| 5,810,398 | A |   | 9/1998  | Matkovich |
| 6,050,978 | A | * | 4/2000  | Orr et al. ................ 604/249 |
| 6,132,403 | A | * | 10/2000 | Lopez ..................... 604/249 |
| 6,299,131 | B1 | * | 10/2001 | Ryan ..................... 251/149.1 |
| 6,902,207 | B2 | * | 6/2005  | Lickliter ................. 285/331 |
| 7,004,934 | B2 | * | 2/2006  | Vaillancourt ............ 604/533 |
| 7,815,614 | B2 | * | 10/2010 | Fangrow, Jr. ............ 604/256 |
| 2003/0060804 | A1 | * | 3/2003 | Vaillancourt ............ 604/533 |
| 2004/0073174 | A1 | * | 4/2004 | Lopez .................... 604/249 |
| 2005/0137566 | A1 | * | 6/2005 | Fowles et al. .......... 604/412 |
| 2007/0066965 | A1 | * | 3/2007 | Coambs et al. ......... 604/533 |
| 2007/0088293 | A1 | * | 4/2007 | Fangrow, Jr. ........... 604/246 |
| 2007/0088294 | A1 | * | 4/2007 | Fangrow, Jr. ........... 604/246 |
| 2007/0225647 | A1 | * | 9/2007 | Luther et al. ........... 604/167.03 |

FOREIGN PATENT DOCUMENTS

EP  0497229  5/1996

* cited by examiner

*Primary Examiner* — Victoria P Shumate
(74) *Attorney, Agent, or Firm* — Saliwanchik, Lloyd & Eisenschenk

(57) ABSTRACT

A connector for enclosed, drip-free, and safe transfer of fluids, comprising an opening and a closure means adapted to close the opening and to establish a tight joint with another connector for transferring fluid between the connectors, further comprising a tube section arranged inside the connector and adapted to be advanced through the opening and out of the connector.

33 Claims, 2 Drawing Sheets

SYSTEM AND METHOD FOR CLOSED, DRIP-FREE, AND SECURE TRANSFER OF FLUIDS

CROSS-REFERENCE TO RELATED APPLICATIONS

The present application is the U.S. National Stage Application of International Patent Application No. PCT/EP2007/003877, filed May 2, 2007, which claims the benefit of German Application Serial No. 102006020845.5, filed May 4, 2006, both of which are hereby incorporated by reference herein in their entirety, including any figures, tables, or drawings.

The instant invention relates to a connector suitable for use in the medical field to transfer fluid in enclosed fashion, drip-free, and safely. The invention also relates to a device comprising two connectors with which any escape or contamination of fluid can be avoided, both while the connectors are interconnected and after their separation. And the invention likewise relates to a corresponding method.

In the preparation and administration of medicines, the starting substances and the medicines obtained must be conveyed between various apparatus, such as receptacles, metering and mixing devices as well as means for administering them, such as syringes and catheters. In cases where handling of the substances presents a health hazard to the persons concerned, any contact or contamination must be avoided at all cost. That is true particularly when dangerous substances, including acids and radioactive material are involved. Due to the temporal variability of medicines or substance compounds marked by isotopes, for example, they must be prepared rather close in space and time to their being administered.

For safeguarding a high degree of product quality, on the other hand, it is desirable to avoid contamination of medicines and their starting substances during and after their preparation, such as while transferring them into means for dosing, preserving, and administering as well as during the administration as such.

Various means used in the manual, semi-automatic and fully automated production are known in the art for transferring, dosing, mixing, and administering medicines or substance compounds which, among others, contain hazardous, in particular poisonous or radioactive substances. For example, so-called Luer Locks are used to connect open tubes or hoses, catheters, or needles which may be closed in addition, if desired, by a respective stopcock or cap. True, tubes provided with Luer Lock component elements may be screwed together or screw-connected to catheters, needles, syringes etc. to obtain a tight connection and prevent their unintentional separation. Nevertheless, they still suffer from the disadvantage that, when disconnecting the joined components, drops may form and persons may come into contact with them. That is risky when hazardous substances are concerned.

It is likewise known to use a septum and a needle for dosing and also to transfer substances. That involves the disadvantage that on puncturing the septum, the needle may cause elevated pressure and drops to develop. As a result, drops may escape from the needle when the needle is removed from the receptacle equipped with the septum, and thus persons may come into contact with the drops. Besides, there is a risk of injury because, as a rule, the needle has a sharp pointed tip.

A common connection between tubes used, in the first place, for the transfer of gaseous fluids is by way of couplings which open automatically when a counterpiece is introduced and close automatically when that counterpiece is withdrawn. Normally, however, only the pressurized end is closed, and there is no protection from subsequent dripping. Besides, contamination may be caused by contact with the outside of the tube or hose sections when disconnected.

The devices described above do provide some protection from contamination of the substances thus handled. However, that is not sufficient to guarantee good product quality.

It is, therefore, an object of the instant invention to provide a connector for fluid transfer and a corresponding method by means of which contact between a fluid which is contained in a tube or receptacle linked to the connector and the surroundings, in particular persons, can be avoided to the greatest possible extent both while fluid communication exists and after the connection has been severed.

This object is met, in accordance with the invention, by:
a first embodiment directed to a connector for enclosed, drip-free, and safe transfer of fluids, comprising an opening and a closure means adapted to close the opening and to establish a tight joint with another connector for transferring a fluid between the connectors, further comprising a tube section arranged inside the connector and adapted to be advanced through the opening and out of the connector;
a second embodiment directed to the connector of the first embodiment, where the closure means is designed such that the tube section may be advanced through and retracted from the same, and the closure means exercises a sealing function whereby the connector is sealed with respect to the tube section when the tube section has been advanced through the closure means;
a third embodiment directed to the connector of the first or second embodiments, where the connector comprises in its interior a carrier holding the tube section;
a fourth embodiment directed to the connector of the third embodiment, where the connector includes a pawl to prevent displacement of the carrier when the connector is separated from the other connector;
a fifth embodiment directed to the connector of the first through fourth embodiments, where the tube section is a needle;
a sixth embodiment directed to a connector for tight, drip-free, and safe transfer of fluids adapted to cooperate with the connector of the first embodiment and receive a movable tube section thereof for establishing a connection for fluid transfer;
a seventh embodiment directed to the connector of the sixth embodiment where the connector comprises an opening and a closure means for closing the opening and designed so that a tube section may be advanced through and retracted out of it, the closure means exercising a sealing function whereby the connector is sealed with respect to the tube section when the tube section has been advanced through the closure means into the connector;
an eighth embodiment directed to the connector of the sixth or seventh embodiments, where the connector comprises a tube section firmly arranged in its interior;
a ninth embodiment directed to the connector of any of the first through eighth embodiments, where the closure means, at the same time, presents a means for establishing a sealed joint between the openings of two connectors for transfer of fluid between the connectors in cooperation with the closure means of another connector;
a tenth embodiment directed to the connector of any of the first through ninth embodiments, where the closure means is a diaphragm;

an eleventh embodiment directed to the connector of the eighth embodiment, where the diaphragm is movably arranged at the connector whereby the location on the diaphragm at which the movable tube section is pushed through the same may be varied;

a twelfth embodiment directed to the connector of any of the first through eleventh embodiments, where the connector comprises a coupling means for establishing a firm, detachable connection with another connector;

a thirteenth embodiment directed to the connector of any of the first through twelfth embodiments, where the connector comprises a means or part of a means which does not permit the connector joined to another connector to be separated from the same nor the joining or coupling of the connector with another connector unless the movable tube section is retracted inside the connector;

a fourteenth embodiment directed to the connector of any of the first through thirteenth embodiments, where the connector is designed as a plug or socket, the plug or socket comprising a means adapted to be joined with or locked to a corresponding means with which the socket or plug, respectively, is provided;

a fifteenth embodiment directed to a connecting device for tight, drip-free, and safe transfer of fluids, comprising two mutually connectable connectors which, when joined, provide a tight connection between openings of the connectors, one of the connectors having an opening and a closure means for closing the opening and one of the connectors comprising a tube section movably arranged inside it and adapted, when the connectors are in joined state, to be advanced through the opening out of the one connector into the other connector to establish fluid communication;

a sixteenth embodiment director to the connector of the thirteenth embodiment, where the closure means is designed to allow a tube section to be advanced through and retracted from it, and that the closure means exercises a sealing function whereby the connector is sealed with respect to the tube section when the tube section has been advanced through the closure means;

a seventeenth embodiment directed to the connector of the thirteenth or fourteenth embodiment, where the connector comprises a closure means at each one of the connectors, these closure means being designed for cooperation to establish a sealed joint between the closure means of the connectors for transferring fluid between the connectors;

an eighteenth embodiment directed to the connector of any of the thirteenth through fifteenth embodiments where the connector not equipped with the movable tube section comprises a fixed tube section with which the movable tube section may be brought into contact to establish a connection for fluid transfer;

a nineteenth embodiment directed to the connector of any of the thirteenth embodiment through the sixteenth embodiment, where the connectors comprise means which permit the coupled connectors to be separated only when the movable tube section is in retracted position inside the connector;

a twentieth embodiment directed to the connector of any of the thirteenth embodiment through the seventeenth embodiment, where one of the connectors is designed as a plug and the other connector as a socket adapted to be joined or coupled to the plug, the plug and socket being configured such that the openings provided in the plug and socket are disposed opposite each other the in joined state;

a twenty-first embodiment directed to the connector of any of the thirteenth embodiment through the eighteenth embodiment, where the connectors each comprise an opening closed by a diaphragm as the closure means;

a twenty-second embodiment directed to the nineteenth embodiment, where the diaphragms of the connectors abut each other when the connectors are coupled, thus forming a sealed joint between the connectors;

a twenty-third embodiment directed to the connector of any of the nineteenth embodiment through the twentieth embodiment, where the movable tube section is a needle and may be moved through the two diaphragms when the connectors are in joined state;

a twenty-fourth embodiment directed to the connector of any of the nineteenth embodiment through the twenty-first embodiment, where the connectors are cylindrical and the diaphragms have circular shape, and the diaphragms together with the respective tube section are arranged concentrically with the longitudinal axis and the openings in the connectors;

a twenty-fifth embodiment directed to the connector of any of the nineteenth embodiment through the twenty-first embodiment, where at least one of the diaphragms is movably arranged at the connector whereby the location on the diaphragm at which the movable tube section is pushed through the same may be varied;

a twenty-sixth embodiment directed to a method of establishing fluid communication between two connectors at least one of said connectors having an opening which is closed by a closure means and one of said connectors including a movable tube section, comprising the steps of putting the connectors together and establishing a sealed joint between them, and advancing the tube section from one connector through the openings of both connectors into the other connector; and a twenty-seventh embodiment directed to the method of the twenty-sixth embodiment, where the closure means is a diaphragm and the movable tube section is a needle which is passed through the diaphragm between the two joined connectors.

According to the invention a connector for enclosed, drip-free, and safe fluid transfer is provided which comprises an opening and a closure means to close the opening and establish a tight joint with another connector for transferring fluid between the connectors and which further comprises a tube section arranged inside the connector and adapted to be advanced through the opening and out of the connector.

The connector according to the invention is sealable so that fluid contained in a receptacle or tube attached to the connector can be prevented from escaping as well as from becoming contaminated. Fluid communication as such for transfer of fluid from this connector into another connector or receptacle which may be joined to this first one is established by a tube section which is movably arranged in the connector and can be advanced out of the connector into a second connector or any other receptacle joined to the same. Preferably, the connection through the tube section is not made until the connectors have been sealed to each other and the closure means has been opened. To sever the connection, it is preferred first to return the movable tube section into the one connector, thereafter the closure means is closed, and only then is the connector separated from the other connector or receptacle linked to it. In this manner, neither can fluid escape which may have remained in the movable tube section, for example, nor can the fluid become contaminated by the surrounding atmosphere.

Escape of any residual fluid from the tube section due, for instance, to elevated pressure inside the tube section, or any adherence of fluid to the outside of the tube section can be prevented to the greatest possible extent with the device according to the invention since it is assured by the closure means that the tube section will not be accessible either before the joining with another connector or in the joined state of two connectors nor even after having separated the two connectors. Vice versa, the fluid is protected from contamination by the surroundings and may be employed also for aseptic purposes.

According to one embodiment of the invention the closure means is designed so that a tube section may be advanced through the same and retracted from it. The closure means, at the same time, exercises a sealing function whereby the connector is sealed with respect to the tube section while the tube section is moved back and forth through the closure means.

With a closure means thus devised, the connector stays sealed from the outside atmosphere by the closure means even when the tube section is in its forward position. Fluid may leave the connector through the tube section alone. The sealing function between the tube section and the closure means serves the additional purpose of wiping off fluid adhering to the outside of the tube section when the tube section is retracted through the closure means. Therefore, the fluid cannot get into the connector nor can it be carried out of the same. In accordance with another embodiment, the connector houses a movable carrier in its interior, and the tube section is arranged on this carrier. In one embodiment, the closure means is a diaphragm or septum while the tube section is a needle. However, it is conceivable also to have the closure means embodied by a mechanical closure means similar to an optical central shutter or any other pivotable or tiltable closure means.

The connector according to one embodiment may comprise a pawl. The pawl serves to prevent displacement of the carrier when the connector is disconnected from the other connector. Thus the risk of injury by the needle advancing out of the connector, when the latter is not joined with another connector, may be prevented.

The invention, moreover, offers a connector for enclosed, drip-free, safe fluid transfer, free of contamination, designed to cooperate with a connector according to the invention including the movable tube section in its interior, as specified above, and to receive that movable tube section so as to provide fluid communication.

According to a preferred embodiment, the second connector likewise may comprise a closure means to close the opening and devised so that a tube section may be advanced through the same into the connector and withdrawn from the connector. This closure means, too, may have a sealing function by which the connector is sealed with respect to the tube section when the latter is advanced or retracted through the closure means into and out of the connector, respectively.

According to another preferred embodiment, the second connector comprises a tube section firmly mounted inside the connector and adapted to be connected to the movable tube section of the first connector to provide a fluid transfer connection which preferably is sealed towards the outside.

The provision of closure means on both connectors offers a particularly high degree of certainty that the surroundings will not become contaminated by a fluid from inside a connector and that the fluid will not become contaminated by substances in the surrounding atmosphere. This is so because each connector is closed in itself and the issuing of fluid or penetration of contaminating substances affecting the product quality can be prevented even if the connectors are not united. By its sealing function with respect to the tube section, the closure means additionally contributes to avoiding that fluid adhering to the outside of the tube section gets out of one of the connectors to the outside when the tube section is displaced from one connector into the other and vice versa. In this manner, the external surfaces of the connectors will be free of residual fluid even after the connectors have been disconnected.

In accordance with yet another embodiment, the closure means devised for cooperation with a closure means, preferably having the same structure, of another connector, also presents a means for forming a tight joint between the openings of two connectors. To achieve that, the closure means according to one embodiment may be implemented in the form of a diaphragm or septum which covers the opening of a connector and comes to lie against a diaphragm of another connector when two connectors are joined.

Thereby, the risks of fluid issuing and of fluid becoming contaminated can be further reduced because an additional sealing means is realized by the mutual action of the closure means, in addition to the tube section which is isolated from the connector. This additional means of sealing preferably is constituted as the connectors are being joined, in other words before the tube section is advanced into the second connector for transferring fluid. In accordance with an alternative embodiment, this additional seal formed by the cooperating closure means may be obtained by a separate means, such as a sealing ring on one or both connectors.

According to an advantageous embodiment, the diaphragm is movably mounted on the connector so that the location on the diaphragm at which the tube section is pushed through the same may be varied. To that end, the diaphragm preferably is mounted so as to be rotatable on the connector. Alternatively, the diaphragm also might be displaceable. When the diaphragm or septum is pierced by the tube section, embodied for instance by a needle, an aperture results in the diaphragm. As the material is elastic, this aperture closes again automatically when the tube section is withdrawn. Repeated use, however, may cause wear of the diaphragm and reduce its density so that the diaphragm may need to be replaced. If a rotatably mounted diaphragm is mounted in such a way that its axis of rotation is offset from the longitudinal axis of the needle the location where the needle pierces the diaphragm becomes variable and, consequently, the lifetime of the diaphragm advantageously may be prolonged. A respective device used for displacing or rotating the diaphragm could be controlled automatically. For example, the diaphragm could be shifted or turned automatically through a certain distance when a certain use rate is attained. A simpler embodiment could comprise a manually displaceable or rotatable diaphragm which might include index positions, if desired. In this manner, certain distances or degrees of shifting the diaphragm could be predetermined.

According to yet another embodiment, the connector comprises a coupling means to make a firm, detachable connection with another connector. Any unintended severing of the connection, especially during transfer of a fluid thus is prevented. The coupling means, for instance, may be devised as a screw connection, in particular a Luer-Lock or bayonet catch or any other suitable means of connection which may be of the automatically catching or locking type, if desired.

According to yet another embodiment, the connector comprises a means or part of a means which does not allow the connector, while coupled to another connector, to be separated from the other connector nor does it allow the joining or coupling with another connector, unless the movable tube section is in retracted position inside the connector.

Consequently, separation of two interconnected connectors cannot be accomplished unless the tube section is withdrawn into one of the connectors behind the closure means, especially in a way so as not to be accessible from outside. An escape of fluid from one of the connectors thus can be prevented, and contamination by fluid either contained in the tube section or adhering to the external surface of the tube section likewise is avoided. As the connectors cannot be separated while the tube section projects from one of the connectors the risk of an injury caused by the tube section in the form of a needle is substantially excluded, and the fluid in the connectors can be prevented from becoming contaminated.

According to yet another embodiment, the connector is designed as a plug or a socket. The plug and socket, respectively, comprise a means devised for linking to or becoming locked in a corresponding means provided on the socket and plug, respectively. The provision of suitable complementary insertion means both on the plug and socket will assure easy assembly and a firm connection between connectors while, at the same time, aligning the openings of the connectors and of the movable tube section with respect to the connector.

According to yet another embodiment, the connector comprises a tube section of which the diameter is less than 5 mm, preferably less than 2 mm, especially preferred being less than 1 mm. The outer diameter of the tube section preferably is smaller than the opening in the connector so that there will be no contact with the opening when the tube section is pushed forward out of the connector. Preferably, the outer diameter of the tube section is selected to be much smaller than the diameter of the opening.

The connector according to the invention is suitable for use with any kind of fluid. It is designed in particular for the transfer of substance compounds containing medical substances, especially radioactive substances, and medicines.

A connecting device for enclosed, drip-free, and safe transfer of fluids likewise is provided by the invention. It comprises two interconnectable connectors which, when joined, provide a tight connection between the openings of the connectors. One of the connectors has an opening and a closure means to close the opening and includes a movable tube section which is arranged inside the connector and, with both connectors joined, can be moved forward from the connector through the opening into the other connector, thus offering fluid communication.

The connecting device according to the invention makes sure that the connection for fluid transfer between two connectors is safe. First, a connection between the connectors can be made by mechanically joining the two, then pushing forward the movable tube section out of the one connector into the other one forms the conduit proper for transfer of fluid. Contamination by fluid inside or on the external surface of the retracted tube section can be prevented by a closure means with which the connector is equipped. Moreover, high product quality can be guaranteed by the connecting device according to the invention since fluid contamination by substances from the surrounding atmosphere can be avoided. The connecting device according to the invention may be used also for aseptic purposes.

With a preferred embodiment the connecting device is realized in such a way that a tube section may be advanced through the same and retracted from it while the closure means, in addition, fulfills a sealing function. The closure means thus seals the connector from the tube section not only during the advancing and retracting movements of the tube section but also while the tube section is in its advanced position.

The sealing function of the closure means has the further effect that any fluid adhering to the outside of the tube section is wiped off when the tube section is reciprocated, rather than escaping from the connector to the outside. The closure means may be implemented, for example, by a diaphragm or septum mounted on the opening of the connector. Moreover, the connecting device may be furnished with a closure means each on the connectors. These closure means cooperate to assure a tight joint between the openings in the connectors for transferring a fluid. The closure means may be realized by two diaphragms or septa which are mounted on the connectors and come to be pressed together as the connectors are joined.

In this manner it is assured that fluid may neither issue from the connecting device to the outside nor may fluid become contaminated once the connectors are joined. Alternatively, the sealing function provided by this embodiment of the closure means might be obtained by an independent sealing means, such as a sealing ring provided on one or both of the connectors.

In accordance with yet another embodiment, the connector without the movable tube section includes a fixed tube section, and the movable tube section may be moved into contact with the fixed tube section to establish fluid communication. To accomplish that, the tube sections preferably have diameters which permit mutual insertion, in other words the outer diameter of one tube section corresponds to the inner diameter of the other tube section. Alternatively or additionally, another sealing means may be provided at one or both tube sections.

According to yet another embodiment, the connectors comprise means which permit coupling of the connectors or uncoupling of joined connectors only when the movable tube section is in its retracted position inside the connector. In this manner, unintentional severing of the connection between the connectors can be prevented while the tube section of one connector is in its advanced position in the other connector. At the same time, contamination by fluid which either may adhere to the outside surface of the tube section or be contained inside the tube section is excluded, just like injuries caused by the tube section.

According to yet another embodiment, one of the connectors is designed as a plug, while the other one is a socket adapted to be connected to or coupled with the plug. The configuration of plug and socket is such that the openings provided in both of them come to be positioned opposite each other upon joining. The specific shaping of plug and socket allows the connectors to be put together quickly.

According to yet another preferred embodiment, the connectors each comprise an opening closed by a respective diaphragm which acts as the closure means. Use of a diaphragm is advantageous in that it is inexpensive and may be employed both as the closure means and sealing means. Where a diaphragm is provided at the opening of each connector their mutual abutment will form a tight joint between the connectors if, for instance, the diaphragms are made of rubber. This tight joint will remain intact also with the tube section in advanced position. Due to the fact that the diaphragms are firmly pressed against each other it is essentially excluded, too, that the diaphragm surfaces located at the outside of the connectors become contaminated. Opening and closing of the closure means is effected by piercing of the diaphragm with a sharp needle. The diaphragm also acts as sealing means with respect to the tube section, whereby fluid adhering to the tube section is retained in the connector when the needle is withdrawn.

The tube section according to one embodiment may be a needle disposed concentrically with the opening of the connector. When two connectors have been joined the needle may be pushed forward and drawn back through both diaphragms.

The tube section may have a diameter of less than 5 mm, preferably less than 2 mm, less than 1 mm being especially preferred.

Moreover, the shape of the connectors may be cylindrical while the diaphragms may be circular, and the diaphragms together with the respective tube section may be arranged concentrically with respect to the longitudinal axis of the joined connectors or of their openings.

According to another advantageous embodiment, at least one diaphragm is arranged to be movable on the connector. Hereby the place at which the tube section is pushed forward through the diaphragm may be varied. To accomplish that, the diaphragm preferably is mounted rotatably on the connector. Alternatively, it might also be arranged to be displaceable. Repeated piercing of the diaphragm or septum by the tube section embodied, for instance, by a needle, may cause wear and reduce the density of the diaphragm. An advantageous extension of the lifetime of the diaphragm is obtainable if the diaphragm is arranged to be rotatable or displaceable either manually or automatically so that the diaphragm piercing location may be varied.

Furthermore, a method is provided according to the invention to establish fluid communication between two connectors, at least one of the connectors having an opening closed by a closure means, and one of the connectors including a movable tube section. The method comprises the steps of putting the connectors together and establishing a tight joint between them and advancing the tube section from one connector through the openings of both connectors into the other connector. According to an embodiment, the closure means may be a diaphragm and the movable tube section a needle which is passed through the diaphragm between the two joined connectors. The method according to the invention is useful for enclosed, drip-free, and safe transfer of fluids and for aseptic applications. Thus, a high degree of safety as regards hazardous substances coming into contact with people as well as maintenance of excellent product quality can be assured.

The invention will be described further, by way of example, with reference to the accompanying drawings, in which.

Figure 1:
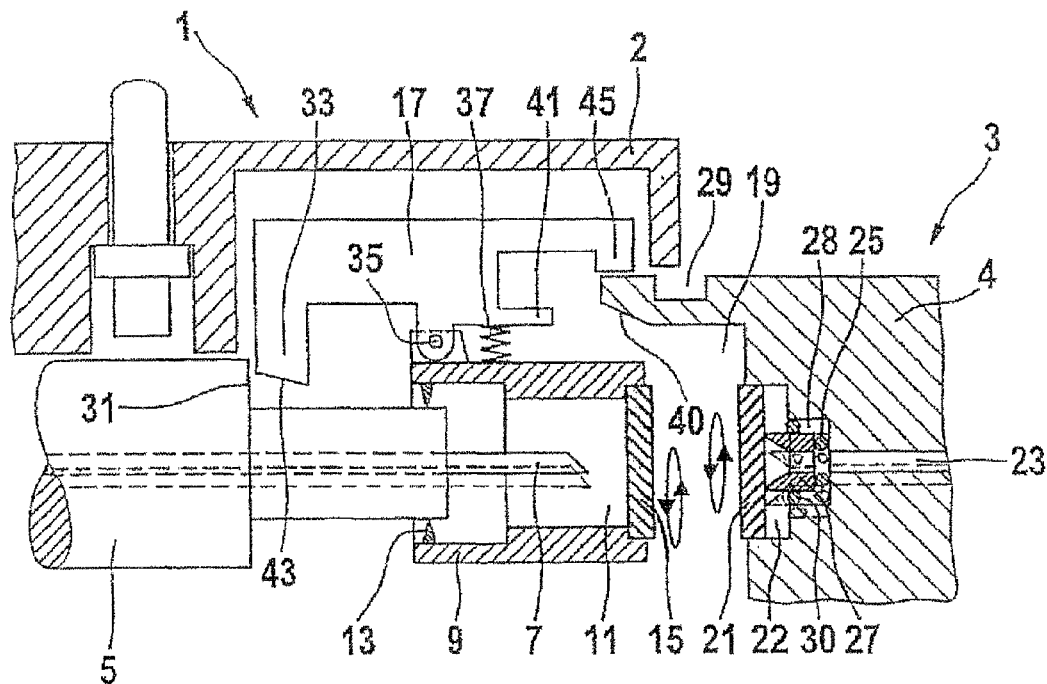
FIG. 1 is a diagrammatic cross-sectional illustration of an embodiment of a connecting device comprising two connectors, shown in non-joined state.

Reference will be made in the description below to FIGS. 1 to 3. As may be taken from the drawing, the connecting device according to the invention comprises a first connector embodied by a plug 1 having a plug housing 2, and a second connector configured as a socket 3. While the drawing illustrates only the upper part of the plug 1 and socket, the plug housing 2 in fact encloses the entire plug 1. A receptacle, hose or tube, catheter, a medical apparatus, etc. may be attached to the plug and socket, and the plug and socket may be integrated firmly into such an apparatus. A tube section and a needle 7, respectively, mounted on a displaceable needle carrier 5 is provided in the interior of the plug 1. In its interior, the plug 1 further comprises a housing portion 9 which ends in an opening 11 and in which the needle carrier 5 is arranged for displacement, being surrounded by the housing portion. The housing portion 9 serves as guide means for the needle carrier 5 and has an inner diameter corresponding to the outer diameter of the needle carrier. Together with the needle 7 it supports, the needle carrier 5 is movable between the retracted position, as shown in FIG. 1, and an advanced position illustrated in FIG. 3. The needle carrier 5 is sealed with respect to the housing portion 9 by a sealing means, for example, a sealing ring 13. Moreover, a diaphragm 15 is disposed at the opening 11 so as to close the same. The diaphragm 15 preferably is a septum made of rubber. The plug 1 also comprises a pawl 17 to prevent displacement of the needle carrier 5 when the plug 1 is not connected to the socket 3. The functioning of the pawl 17 will be described in greater detail below.

The socket 3, likewise illustrated in part only in the drawing, comprises a receiving portion 19, configured as a depression, to take up the housing portion 9 which protrudes from the plug 1. A diaphragm 21 which corresponds in structure and arrangement to the diaphragm 15 mounted on the plug 1 is provided in the receiving portion 19 to seal an opening 22 formed in the socket 3. Behind the diaphragm 21, a tube section 23 is formed and fixedly disposed in the socket 3. It is sealed with respect to the socket 3 by a sealing ring 25. In front of and concentrically with the tube section 23, the socket 3 further comprises an insertion guide means 27 for the movable needle 7 of the plug 1. The insertion guide means 27 is mounted in a respective recess 28 formed in the socket 3. The insertion guide means 27, too, is sealed with respect to the socket 3 by a sealing ring 30. A locking groove 29 is formed in the outer circumference of the socket housing 4 of socket 3 to cooperate with the pawl 17. The function and mode of action of the locking groove, together with the pawl 17, will be described in greater detail below.

When they are not joined, both connectors 1, 3 are sealed from the outside atmosphere so that fluid may not escape from the connectors to the outside, nor may fluid become contaminated through the connectors. That assures good product quality.

The plug housing 2, the needle carrier 5, and the socket housing 4 preferably are of cylindrical, symmetrical shape. The opening 11, diaphragm 15, needle carrier 5, and the needle 7 are arranged concentrically with the axis of the plug 1. On the other hand, the diaphragm 21, tube section 23, and the insertion guide means 27 are arranged concentrically with the longitudinal axis of the socket 3. The plug housing 2 and the socket housing 4 also may be designed to have any other shape, such as that of a parallelepiped. The plug 1 and the socket 3, or parts thereof, may be made of plastics, for example ABS, PI, PE, or PP, or of metal or any other suitable material.

A description of how the connectors are joined and separated, respectively, will be given below with reference to FIGS. 1 to 3. As FIG. 1 shows, initially the needle carrier 5 in the plug 1 is in retracted position, with a shoulder 31 of the needle carrier 5 abutting against a first blocking portion 33 of the pawl 17, whereby the needle carrier 5 is prevented by the pawl 17 from moving forward. The pawl is supported for tilting movement about an axis 35 and biased by a spring 37 which keeps the pawl in a position at which forward movement of the needle carrier 5 is blocked.

Figure 2:
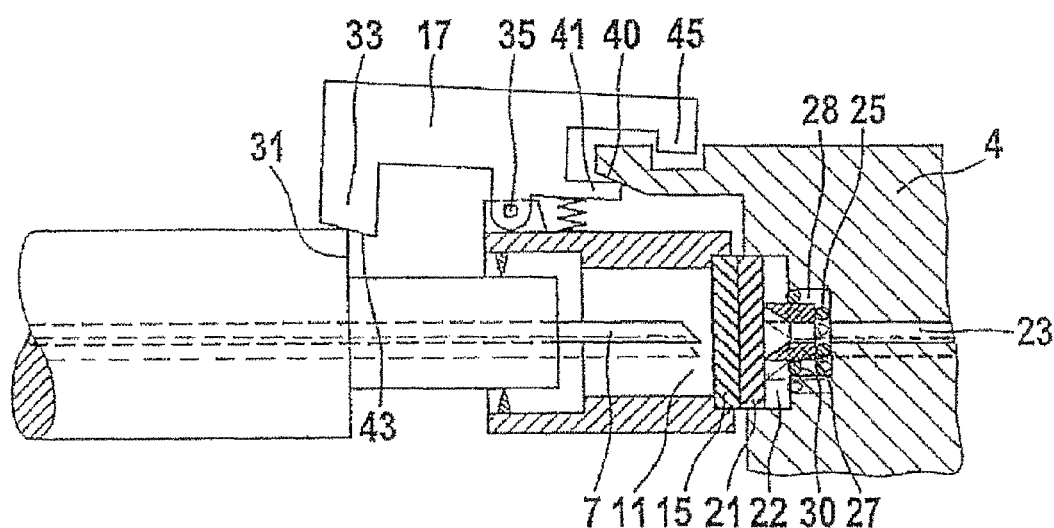
FIG. 2 is a cut-out of FIG. 1 showing the connecting device in the phase of joining the connectors.

As the socket moves forward in the direction of the plug 1, when plug 1 and socket 3 are being joined, the inclined surface 40 formed at the socket housing 4 comes into contact with the nose 41 of the pawl 17, as may be seen in FIG. 2. Hereby the pawl 17 is pivoted in clockwise sense against the bias of the spring 37. That breaks the engagement between the blocking portion 33 of pawl 17 and the needle carrier 5. The socket 3 is moved forward until the diaphragms 15 and 21 come to lie against each other, as illustrated in FIG. 2. This mutual abutment of the diaphragms 15, 21 produces a tight joint between the opening 11 of the plug 1 and the opening 22 of the socket 3. In this position the plug 1 and the socket 3 may be fixed to each other by means (not shown) with which they each are provided and which come to act together, such as component parts of a screw connection, especially a Luer-Lock or bayonet type catch. Such means, however, are not absolutely required for the functioning of the invention; they may also be dispensed with.

During assembly of the plug 1 and socket 3, the pivoting motion of the pawl 17 in clockwise sense causes the first blocking portion 33 to be raised above the shoulder 31 of the needle carrier 5. Therefore, the needle carrier 5 now may be pushed forward in the direction of the opening 11 of the plug 1. During this forward movement of the needle carrier 5, the shoulder 31 engages the inclined surface 43 of the first blocking portion 33 of the pawl, hereby the pawl is rotated further in clockwise sense as the needle carrier 5 advances. This causes a second blocking portion 45 of the pawl 17 to enter into engagement in the locking groove 29 of the socket 3. The locking engagement of the second blocking portion 45 of the pawl 17 in the locking groove 29 of the socket 3 prevents plug 1 and socket 3 from becoming disconnected when the needle carrier 5 is in this forward position.

Figure 3:
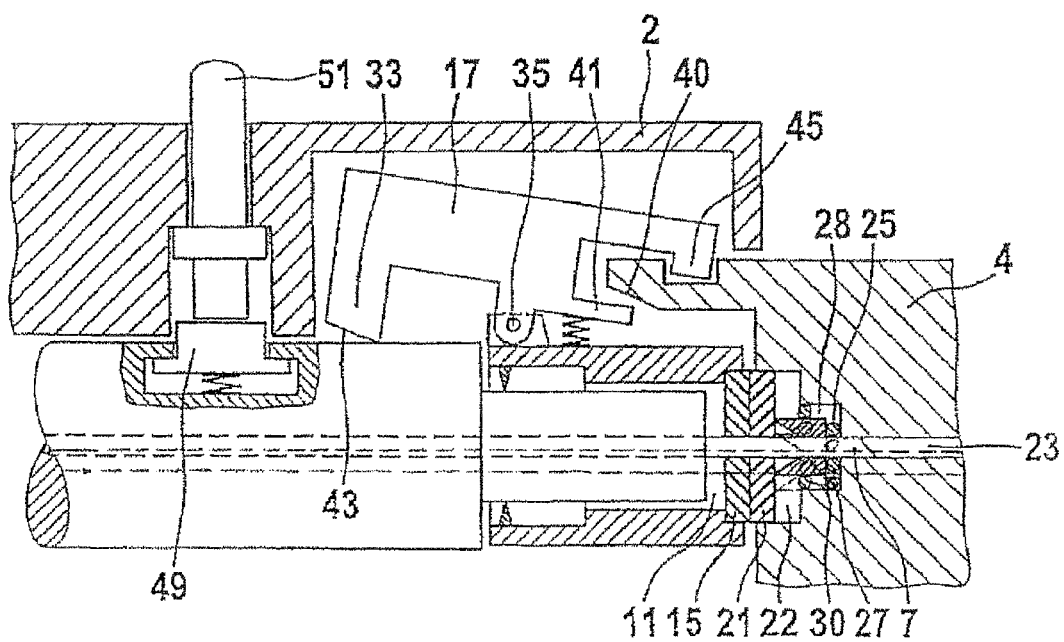
FIG. 3 shows the connecting device of the embodiment with the connectors in joined state.

Now the needle carrier 5 may be pushed through both diaphragms 15, 21 of plug 1 and socket 3 into the tube section 23 formed in the socket 3 until the shoulder 31 of the needle carrier 5 abuts against the housing portion 9 of the plug housing 2, as shown in FIG. 3. The connecting device thus is ready for fluid to be transferred from the plug 1 into the socket 3 or vice versa.

The outer diameter of the tube section 7 of the plug 1 is selected in consideration of the inner diameter of the tube section 23 of the socket 3 so as to obtain a sealed connection between the tube sections. The tightness of the tube sections 7, 23 when connected may be enhanced by an additional sealing means provided on one or both tube sections.

Independently of the connection between the tube sections 7, 23, a tight joint is obtained between the plug housing 2 and the socket housing 4 by the diaphragms 15, 21 abutting against each other. Hereby the connecting device is sealed in addition from the outside. The connecting device according to the invention is suitable to warrant enclosed, drip-free, and safe transfer of fluids between two connectors. On the one hand, it prevents contact between a hazardous, especially a poisonous, etching, and/or radioactive fluid and persons who are handling such fluids and, on the other hand, it keeps contaminants, such as gaseous, liquid, or solid substances of the environment away from the fluids.

The plug further is provided with a spring-biased stop 49 which prevents unintended withdrawal of the needle carrier 5 into the plug 1. The stop 49 may be released by pressing a switch 51.

The connectors 1, 3 are disconnected by the same procedure as applied for putting them together, but in opposite order. First, the stop 49 is released by pressing the switch 51 so that the needle carrier 5 may be retracted into the plug 1. If desired, a mechanism (e.g. a spring mechanism) may be provided on the plug 1 by means of which the needle carrier 5 travels back automatically into the plug housing 2. At this time, the needle is pulled back through both septa. Due to the sealing effect, specifically between the septum provided on the socket 3 and the needle, any fluid adhering to the outside of the needle is wiped off and remains inside the socket 3. As the needle 7 is retracted behind the septum of the plug 1, the first blocking portion 33 of the pawl 17 slides over the shoulder 31 of the needle carrier. Thus the pawl is pivoted in counterclockwise sense under the action of the spring, and the second blocking portion 45 of the pawl is disengaged from the locking groove 29. Thus the socket 3 and the plug 1 are separable. First however, the additional stop means described above which acts between socket and plug must be released.

The needle 7 in the plug 1 is located behind septum and, therefore, contamination of the outside of the plug 1 by any fluid drops which may have remained in the needle is excluded. Contamination of the outside of the septa on withdrawal of the needle likewise is avoided because, when the plug 1 and the socket 3 were joined, the two septa were moved into mutual abutment.

The embodiment of the invention described may be subjected to numerous alterations and modifications without leaving the scope of the invention. For example, it is conceivable to realize the pawl and the entire locking mechanism, respectively, in a different manner. Other than with the embodiment shown, the pawl might be mounted on the socket just as well. Also, the needle carrier may be provided on the socket rather than in the plug 1. The diaphragms and septa, respectively, described above may be replaced by mechanical locking means, e.g. central closure means. Finally, plugs and sockets, respectively, are conceivable which do not include all of the features and properties described. The plug, for example, instead of being connected to the socket might be coupled directly with a hose, tube, or a receptacle not including a tube section or diaphragm.

The properties and features of the invention disclosed in the specification above may be important to the invention, either individually or in any combination.

The invention claimed is:

1. A connector for enclosed, drip-free, and safe transfer of fluids, comprising:
   an opening; and
   a closure means adapted to close the opening and to establish a tight joint with a second connector for transferring a fluid between the connector and the second connector, wherein the connector comprises in its interior a carrier holding a tube section so that the tube section can be advanced through the opening out of the connector, and a pawl, the pawl being movable between a first position in which the pawl prevents an advancement of the carrier in a direction towards the opening when the connector is separated from the second connector and a second position in which the tube section can be advanced in the direction towards the opening.

2. The connector according to claim 1, wherein the closure means is designed such that the tube section may be advanced through and retracted from the same, and the closure means exercises a sealing function whereby the connector is sealed with respect to the tube section when the tube section has been advanced through the closure means.

3. The connector according to claim 1, wherein the tube section is a needle.

4. The connector according to claim 1, wherein the closure means is a diaphragm.

5. The connector according to claim 4, wherein the diaphragm is movably arranged at the connector, whereby the location on the diaphragm at which the movable tube section is pushed through the same may be varied.

6. The connector according to claim 5, wherein a second diaphragm is movably arranged at the second connector, whereby the location on the second diaphragm at which the movable tube section is pushed through the same may be varied.

7. The connector according to claim 1, further comprising a coupling means for establishing a firm, detachable connection with the second connector.

8. The connector according to claim 1, further comprising a means or part of a means which does not permit the connector joined to the second connector to be separated from the same nor the joining or coupling of the connector with the second connector unless the movable tube section is retracted inside the connector.

9. The connector according to claim 1, wherein the connector is designed as a plug, the plug comprising a means adapted to be joined with or locked to a corresponding socket with which the plug is provided.

10. A connector for tight, drip-free, and safe transfer of fluids, wherein the connector is adapted to cooperate with a second connector wherein the second connector comprises:
a second opening and a second closure means adapted to close the second opening and to establish a tight joint with the connector for transferring a fluid between the second connector and the connector, wherein the second connector comprises in its interior a carrier holding a tube section so that the tube section can be advanced through the second opening out of the second connector, and comprises a pawl, the pawl being movable between a first position in which the pawl prevents an advancement of the carrier towards the second opening when the connector is separated from the second connector and a second position in which the tube section can be advanced in the direction towards the second opening,
wherein the connector is adapted to receive the movable tube section of the second connector for establishing a connection for fluid transfer.

11. The connector according to claim 10, further comprising an opening and a closure means for closing the opening and designed so that the tube section may be advanced through and retracted out of the closure means, the closure means exercising a sealing function whereby the connector is sealed with respect to the tube section when the tube section has been advanced through the closure means into the connector.

12. The connector according to claim 11, wherein the closure means is adapted for establishing a sealed joint between the opening of the connector and the second opening of the second connector for transfer of fluid between the connector and the second connector in cooperation with the closure means of the second connector.

13. The connector according to claim 11, wherein the closure means is a diaphragm, wherein the second closure means is a second diaphragm.

14. The connector according to claim 13, wherein the diaphragm is movably arranged at the connector, whereby the location on the diaphragm at which the movable tube section is pushed through the same may be varied.

15. The connector according to claim 14, wherein the second diaphragm is movably arranged at the second connector, whereby the location on the second diaphragm at which the movable tube section is pushed through the same may be varied.

16. The connector according to claim 10, further comprising a tube section firmly arranged in its interior.

17. The connector according to claim 10, further comprising a coupling means for establishing a firm, detachable connection with the second connector.

18. The connector according to claim 10, wherein the second connector comprises:
a means which does not permit the second connector joined to the connector to be separated from the same nor the joining or coupling of the second connector with the connector unless the movable tube section is retracted inside the second connector.

19. The connector according to claim 10, wherein the connector is designed as a socket, the socket comprising a means adapted to be joined with or locked to a corresponding plug with which the socket is provided.

20. A connecting device for tight, drip-free, and safe transfer of fluids, comprising two mutually connectable connectors being adapted to provide a tight connection between a first opening of a first connector of the two connectable connectors and a second opening of a second connector of the two connectable connectors when in a joined state, wherein the first connector comprises a first closure means for closing the first opening and in its interior a carrier holding a tube section so that the tube section can be advanced through the first opening out of the first connector into the second connector when the first and second connectors are in the joined state for establishing a fluid connection, wherein the first connector further comprises a pawl, the pawl being adjusted to prevent an advancement of the carrier in a direction towards the first opening when the first connector is separated from the second connector, and being disengageable from the carrier when the first connector and the second connector are in the joined state.

21. The connecting device according to claim 20, wherein the first closure means is designed to allow the tube section to be advanced through and retracted from the first closure means, and that the first closure means exercises a sealing function whereby the first connector is sealed with respect to the tube section when the tube section has been advanced through the first closure means.

22. The connecting device according to claim 20, wherein the second connector comprises a second closure means the first and second closure means being designed for cooperation to establish a sealed joint between the first and second closure means for transferring fluid between the first and second connectors.

23. The connecting device according to claim 22, wherein the first closure means is a first diaphragm and the second closure means is a second diaphragm.

24. The connecting device according to claim 23, wherein the first and second diaphragms abut each other when the first and second connectors are in the joined stated, thus forming a sealed joint between the first and second connectors.

25. The connecting device according to claim 23, wherein the tube section is a needle and may be moved through the first and second diaphragms when the first and second connectors are in the joined state.

26. The connecting device according to claim 23, wherein the first and second connectors are cylindrical and the first and second diaphragms have circular shapes, wherein the first diaphragm is arranged concentrically with a longitudinal axis and the first opening, and wherein the second diaphragm is arranged concentrically with the longitudinal axis and the second opening.

27. The connecting device according to claim 26, wherein the second connector comprises a fixed tube section with which the movable tube section may be brought into contact to establish a connection for fluid transfer, wherein the tube section and the fixed tube section are arranged concentrically with the longitudinal axis.

28. The connecting device according to claim 23, wherein at least one of the first and second diaphragms is movably arranged at the corresponding at least one of the first and second connector whereby the location on the at least one of the first and second diaphragm at which the tube section is pushed through the same may be varied.

29. The connecting device according to claim 20, wherein the second connector comprises a fixed tube section with which the tube section may be brought into contact to establish a connection for fluid transfer.

30. The connecting device according to claim 20, where the first and second connectors comprise means which permit the first and second connectors in the joined state to be separated only when the tube section is in a retracted position inside the first connector.

31. The connecting device according to claim 20, wherein the first connector is designed as a plug and the second connector is designed as a socket adapted to be joined or coupled to the plug, the plug and socket being configured such that the first opening provided in the plug and the second opening provided in the socket are disposed opposite each other in joined state.

32. A method of establishing fluid communication between two connectors each having an opening, at least one of said two connectors having a closure means which closes the opening, and one of said two connectors including in its interior a carrier holding a tube section and a pawl, the pawl preventing an advancement of the carrier towards the opening when the one of said two connectors is separated from the other connector, the method comprising:
   putting the two connectors together, thereby disengaging the pawl from the carrier;
   establishing a sealed joint between the two connectors; and
   advancing the tube section from the one of said two connectors through the openings of both connectors into the other connector.

33. The method as claimed in claim 32, wherein the closure means is a diaphragm and the movable tube section is a needle which is passed through the diaphragm between the two joined connectors.

* * * * *

UNITED STATES PATENT AND TRADEMARK OFFICE
CERTIFICATE OF CORRECTION

PATENT NO. : 8,372,058 B2  
APPLICATION NO. : 12/299604  
DATED : February 12, 2013  
INVENTOR(S) : Michael Schilp et al.

Page 1 of 1

It is certified that error appears in the above-identified patent and that said Letters Patent is hereby corrected as shown below:

In the Specification

Column 1,
Line 55, "risky when" should read --risky where--.

Column 3,
Line 34, "director to" should read --directed to--.
Line 49, "embodiments where" should read --embodiments, where--.

Column 4,
Line 29, "connectors at" should read --connectors, at--.

In the Claims

Column 14,
Line 41, "in the joined stated" should read --in the joined state--.

Signed and Sealed this
Third Day of June, 2014

Michelle K. Lee
*Deputy Director of the United States Patent and Trademark Office*